(12) United States Patent
Taketoshi et al.

(10) Patent No.: US 7,044,636 B2
(45) Date of Patent: May 16, 2006

(54) METHOD OF MEASURING FAST TIME RESPONSE USING FAST PULSE AND SYSTEM OF THE SAME

(75) Inventors: Naoyuki Taketoshi, Ibaraki (JP); Tetsuya Baba, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/424,933

(22) Filed: Apr. 29, 2003

(65) Prior Publication Data

US 2003/0202556 A1    Oct. 30, 2003

(30) Foreign Application Priority Data

Apr. 30, 2002    (JP)    ............... 2002-128426

(51) Int. Cl.
*G01J 5/08*    (2006.01)
*G01N 25/00*    (2006.01)
*G01N 21/71*    (2006.01)

(52) U.S. Cl. ................ 374/45; 374/130; 356/446; 356/432

(58) Field of Classification Search ........... 374/57, 374/45, 4–5, 120, 121, 130, 43–44; 356/630, 356/432, 446, 503
See application file for complete search history.

(56) References Cited

U.S. PATENT DOCUMENTS

| | | | | |
|---|---|---|---|---|
| 4,636,088 A | * | 1/1987 | Rosencwaig et al. | ........... 374/5 |
| 4,874,948 A | * | 10/1989 | Cielo et al. | ............... 250/341.5 |
| 5,258,612 A | * | 11/1993 | Clark et al. | .................. 250/226 |
| 5,287,183 A | * | 2/1994 | Thomas et al. | ............. 348/571 |
| 5,374,122 A | * | 12/1994 | Devitt et al. | ................... 374/45 |
| 5,667,300 A | * | 9/1997 | Mandelis et al. | ............. 374/43 |
| 5,706,094 A | * | 1/1998 | Maris | ........................ 356/432 |
| 5,959,735 A | * | 9/1999 | Maris et al. | ................. 356/632 |
| 6,271,921 B1 | * | 8/2001 | Maris et al. | ................. 356/432 |
| 6,411,390 B1 | * | 6/2002 | Nikoonahad et al. | ....... 356/502 |
| 6,592,252 B1 | * | 7/2003 | Baba | ........................... 374/43 |
| 6,595,685 B1 | * | 7/2003 | Baba et al. | ................. 374/161 |
| 6,712,502 B1 | * | 3/2004 | Zalameda et al. | ............. 374/5 |
| 2003/0012252 A1 | * | 1/2003 | Bender | ........................ 374/32 |

(Continued)

OTHER PUBLICATIONS

Pulse Phase Infrared Thermography. X. Maldague et al. Applied Physics79 (5) Mar., 1996,☐☐pp. 2694-2698.*

*Primary Examiner*—Gail Verbitsky
(74) *Attorney, Agent, or Firm*—Mattingly, Stanger, Malur & Brundidge, P.C.

(57) ABSTRACT

A measuring method eliminates the limitation of the observation time scale controlled of the optical path length, and expands the range of samples of the thermoreflectance method using a pulse laser. The method irradiates an extremely fast light pulse to a sample as a pump light pulse to excite the sample and a probe light pulse to the sample, and observes the temperature variation of the sample by detecting a reflected light from the sample. The method prepares for electrically controllable two pulse lasers: one for exciting the sample, another one for probing, separately. By electrically controlling the difference between the time at which the exciting light irradiates the sample and the time at which the probing light irradiates the sample, the method detects a signal that varies depending on the time difference between the pump pulse and the probe pulse.

30 Claims, 6 Drawing Sheets

U.S. PATENT DOCUMENTS

| | | | |
|---|---|---|---|
| 2003/0165178 A1* | 9/2003 | Borden et al. .................. | 374/5 |
| 2005/0002436 A1* | 1/2005 | Taketoshi et al. ............. | 374/43 |
| 2005/0062971 A1* | 3/2005 | Salnik et al. ................ | 356/432 |
| 2005/0146725 A1* | 7/2005 | Hansen et al. ............... | 356/446 |
| 2005/0213100 A1* | 9/2005 | Murtagh et al. ............ | 356/432 |
| 2005/0225765 A1* | 10/2005 | Nicolaides et al. ......... | 356/432 |

* cited by examiner

METHOD OF MEASURING FAST TIME RESPONSE USING FAST PULSE AND SYSTEM OF THE SAME

FIELD OF THE INVENTION

The present invention relates to a method of measuring a fast time response using a fast pulse, which irradiates an extremely fast light pulse to a sample as a heating light pulse and a probe light pulse to the sample, and thereby observes a temperature change by detecting a reflected light from the sample, and a system of the same.

BACKGROUND OF THE INVENTION

Figure 2:
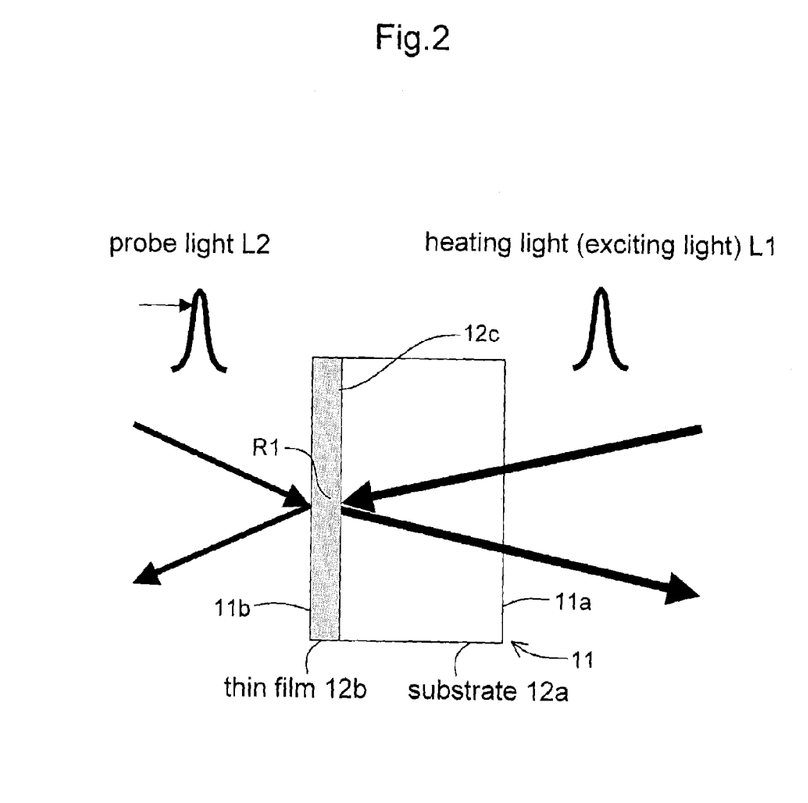
FIG. 2 is a typical chart Illustrating the principle of the picosecond thermoreflectance method.

The picosecond thermoreflectance method is a powerful method to measure a thermal diffusivity of a thin film which is thinner than one micrometer. FIG. 2 illustrates the principle of the picosecond thermoreflectance method. To irradiate an extremely fast light pulse, as a heating light, to a boundary between a substrate and a thin film will cause an instantaneous temperature rise of the boundary, and thereafter the heat diffuses inside the thin film. In order to observe the temperature response of the surface of the thin film, the picosecond (or femtosecond) thermoreflectance method irradiates a probe light pulse onto the surface of the thin film, and observes the surface temperature change of the thin film from the reflectivity change of the probe light that depends on the temperature change. The temperature change per one pulse is about 0.1° C., and the reflectivity change proportional to this temperature change is as small as about one hundred-thousandth.

Figure 3:
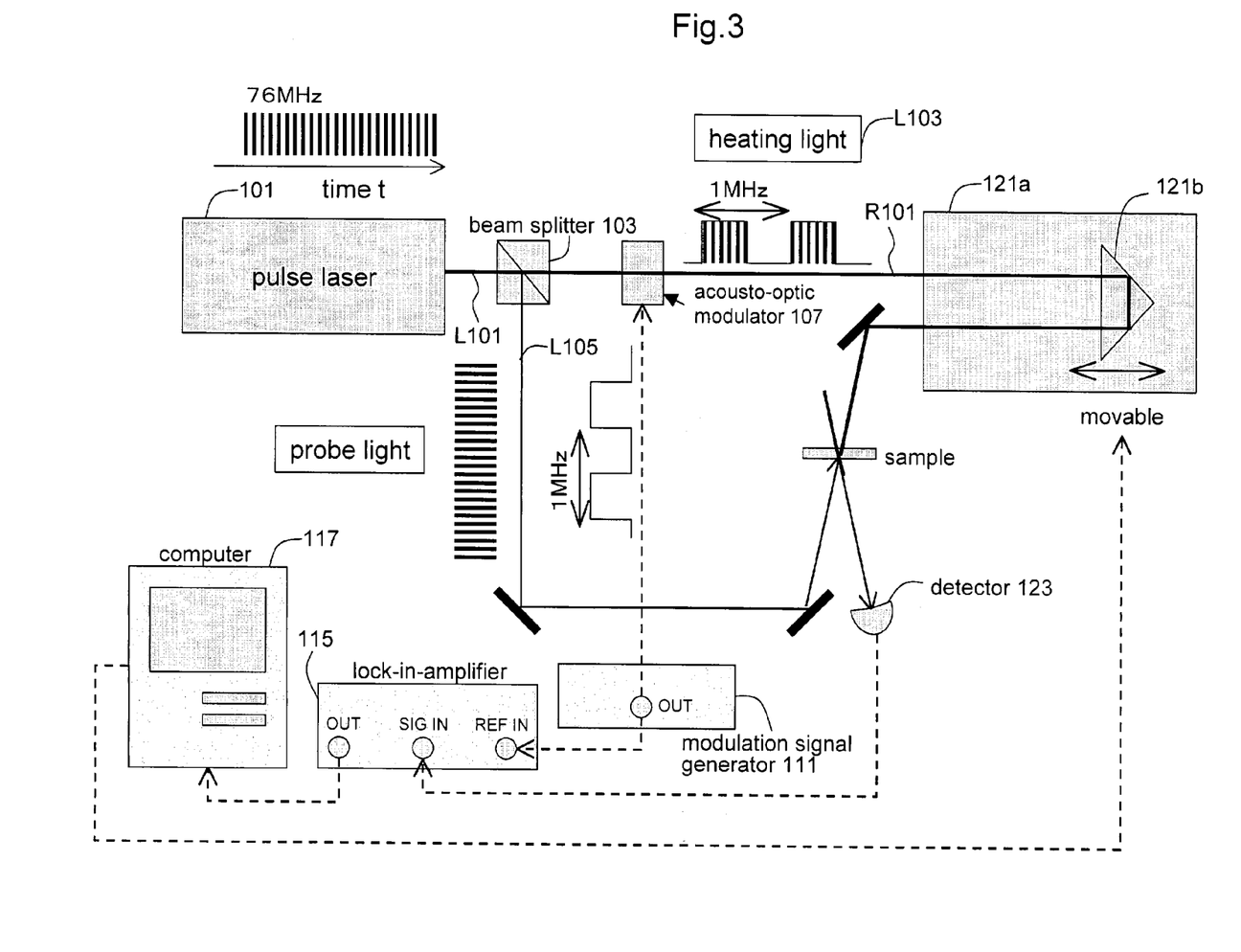
FIG. 3 is a block diagram of the conventional picosecond thermoreflectance method.

FIG. 3 illustrates a block diagram of the conventional thermoreflectance method using a picosecond (or femtosecond) pulse laser. The pulse laser 101 emits a light pulse L101 of which pulse width is 2 picoseconds with a repetition frequency of 76 MHz, and a beam splitter 103 splits the light pulse L101 into a heating light L103 for a sample and a probe light L105.

The intensity of the heating light is modulated by an acousto-optic modulator 107 with 1 MHz, the heating light passes a delay line R101 and heats the surface of the sample. A modulation signal generator 111 generates a signal inputted to the acousto-optic modulator 107, and delivers a part of the output to the reference signal input of a lock-in amplifier 115.

The delay line R101 is made up with a mechanism 121a in which a corner cube retroreflector 121b moves in parallel. By moving the position of the corner cube retroreflector 121b, the method adjusts the time for the probe light pulse L105 reaching the sample against the heating light pulse L103. The modulated heating beam travels through an optical delay line. The corner cube retroreflector can translate over the distance of about 150 mm. To move the corner cube retroreflector 121b by 0.15 mm will change the optical path length by 0.3 mm, which corresponds to one picosecond in terms of the arrival time difference between the pump light pulse and the probe light pulse.

The probe light L105 is focused on the back of an area where the heating light L103 is focused, as shown in FIG. 2, and a reflected light thereof falls on a detector 123 (FIG. 3). A detected signal is led to the signal input of the lock-in amplifier 115.

Figure 4:
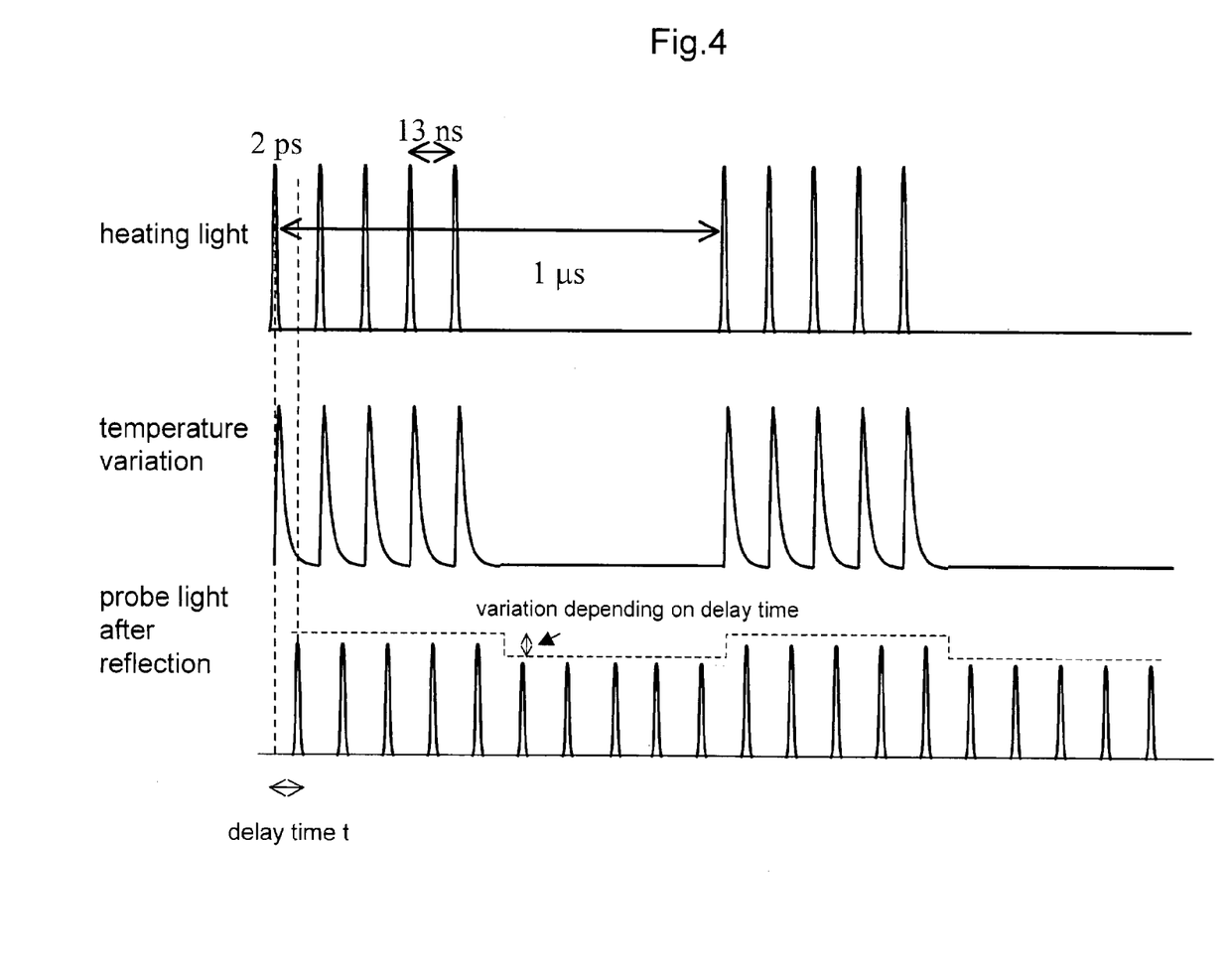
FIG. 4 is a typical chart illustrating the function of a delay line.

Since the reflectivity change proportional to the temperature change is as small as one hundred-thousandth, the lock-in-amplifier 115 detects the components synchronized with the modulation frequency 1 MHz from the detected signal. FIG. 4 illustrates the principle of detecting the temperature response by pulse heating. When the heating light pulse is repeatedly emitted, the surface temperature of the sample changes with the same repetition frequency. If the probe light pulse repeatedly emitted with the same frequency reaches the sample surface with a delay of the time difference t against the heating light L103, it will give an intensity change of the probe light L105 that is proportional to the temperature change after t second from the pulse heating. Besides, since the intensity of the heating light is modulated by 1 MHz, the intensity of the reflected probe light also varies with 1 MHz. To detect the temperature change at a certain delay time t, the components synchronized with the modulation frequency 1 MHz by the lock-in-amplifier 115 is recorded using a computer system 117. The thermoreflectance history curve by pulse heating can be acquired by varying the delay time t of the probe light L105 to the heating light L103.

The picosecond thermoreflectance method is a powerful method in order to observe the thermal properties of a thin film, however there still remains the following problems.

1. When the optical path length is changed, the irradiated area changes due to beam divergence. To move the optical path length by more than 30 cm (equivalent to the time difference of 1 nanosecond) will change the spot area by 10 micrometer, which leads to a drift of the thermoreflectance signal detected by the lock-in-amplifier. From this limitation, the difference in the optical path length has to be within about 30 cm.

2. In case of a thin film material with more than 100 nanometers in thickness, a thin film of low thermal conductivity, and a multi-layered film material having a high boundary thermal resistance, there are some materials that require more than one nanosecond for the temperature to be transmitted from the back to the surface. In such a case, even if the optical path length is moved to the maximum, it is impossible to confirm the steady state of temperature rise by one pulse, which results in difficulty of the quantitative measurement of the thermophysical properties.

In order to carry out the thermal design of semiconductor devices, large-capacity storage media such as optical disks, magneto-optical disks, hard disks, and so forth, or to understand the transport phenomena of the thermal energy in the highly technological multi-layered film such as laminated composite materials, it is essential to know the thermophysical properties of the each layer and the boundary thermal resistances. The conventional picosecond (or femtosecond) thermoreflectance method is likely to be influenced by a slight dislocation of the optical axis that is created in measurement. In case of measuring the thermophysical properties of a comparably thick material (more than 100 nanometers), a multi-layered film material, a low thermal conductivity material, and so forth, which require a comparably long time for the transmission of the thermal energy, it takes more than one nanosecond for the temperature rise on the back side. Accordingly, the method does not present the total understanding of the temperature response, and gives difficulties in the quantitative measurements of thermal diffusivities and boundary thermal resistances.

SUMMARY OF THE INVENTION

The present invention intends to eliminate the limitation of the observation time scale controlled by the optical path length, and to expand a variety of samples of the thermoreflectance method using a pulse laser.

According to one aspect of the invention, the method of measuring a fast time response using a fast pulse Irradiates an extremely fast light pulse to a sample as a light pulse to excite the sample, and on the other hand, it irradiates a probe light pulse to the sample, and thereby observes the temperature response of the sample by detecting a reflected light from the sample. The method prepares for electrically controllable two pulse lasers: one for exciting the sample, and another one for probing, separately. By electrically controlling the difference between the time at which the pump light pulse irradiates the sample and the time at which the probe light pulse irradiates the sample, the method detects a signal that varies depending on the time difference between the pump light pulse and the probe light pulse.

The two pulse lasers emit pulsed lights with the same repetition period, and are able to measure the thermal properties of a thin film by means of the pump-probe method. The two pulse lasers employ a laser that periodically emits a light pulse with a pulse width shorter than a nanosecond. And, the emitting periods of the two pulse lasers can be controlled and stabilized by electrical periodic reference signals.

Synchronizing the periodic reference signal to be sent to the pulse laser for exciting the sample with the periodic reference signal to be sent to the probe pulse laser, the method controls the phase difference between the reference signals to thereby control the time difference between the pump pulse and the probe pulse.

The temperature rise of the sample can be detected by the thermoreflectance method. The method irradiates a pump light pulse on the surface of the sample, and detects a temperature rise on the front surface or the back of the sample. The sample includes a single layer thin film and a multi-layered film.

The invention enable the picosecond thermoreflectance method to apply to a multi-layered film having an boundary between a metal and a non-metal, and materials of low thermal conductivities. Since the method does not give any change to the optical path length, it will not change the irradiation area of the light during measurement. The measurement system of this invention will not require that the pulse width should be some picoseconds or femtoseconds, and the repetition period is optional. This system is applicable not only to thermophysical property measurements but also to various measurements, such as the sound velocity measurement of a thin film by the optical pump probe method, the dynamic Raman spectrometry, transient grating method, and so forth.

DETAILED DESCRIPTION OF THE PREFERRED EMBODIMENTS

Figure 1:
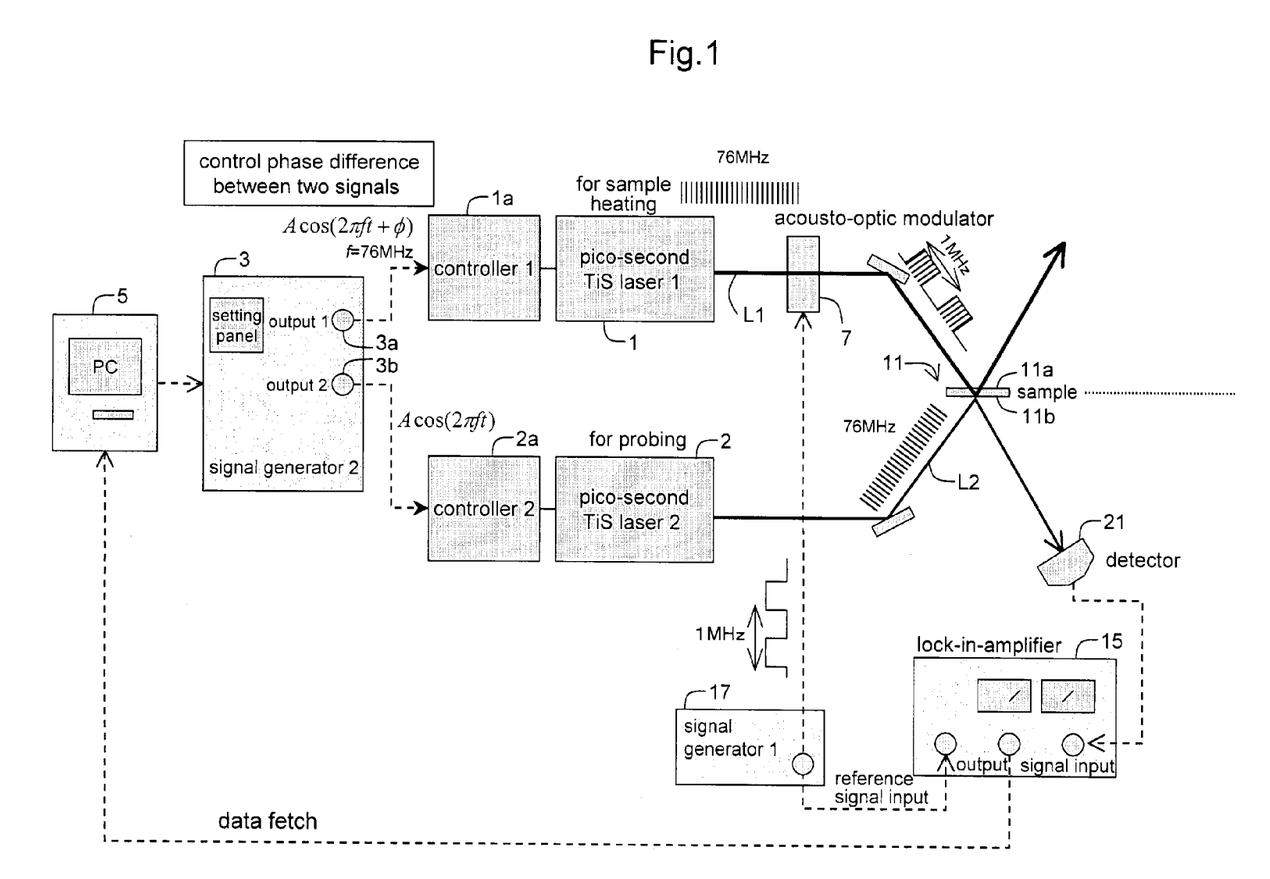
FIG. 1 is a block diagram of a measurement system implemented.

The embodiment will be described based on an illustration. FIG. 1 illustrates a block diagram of a measurement system that embodies the invention. The illustrated measurement system is provided with a heating (exciting) light pulse and a probe light as separate light sources in order to overcome the limitation by using the delay line, and controls the timings of both the light sources emitting the pulsed lights, by electrical signals.

The light sources include picosecond titanium sapphire lasers that generate laser pulses, controllers that control the repetition periods of the pulses to be constant and stable, and a signal generator that generates reference signals used by the controllers.

A picosecond titanium sapphire (TiS) laser 1 is used as a sample heating light, and a picosecond TiS laser 2 is used as a probe light. The pulse width is 2 picoseconds for both, and the oscillation frequency is 76 MHz (repetition period 13.2 nanoseconds). In order to maintain the repetition frequency of the picosecond TiS laser 1 at 76 MHz, a controller 1a controls the cavity length of the picosecond TiS laser 1. The reference signal of 76 MHz for the control is supplied from the output 1 of the signal generator 3. In the same manner, to maintain the repetition frequency of the picosecond TiS laser 2 at 76 MHz, a controller 2a controls the cavity length of the picosecond TiS laser 2. The reference signal of 76 MHz for the control is supplied from the output (2) of the signal generator 3. Since both the heating picosecond pulses and the probe picosecond pulses are synchronized with the each reference signal from the out put (1) and the output (2), respectively, the delay of the heating pulse to the probe pulse is determined by the phase difference between the signal output (1) and the signal output (2). The phase difference between the signal output (1) and the signal output (2) is controllable on the console panel for setting the signal waveform of the signal generator 3, or remotely controllable on a personal computer 5.

This embodiment uses two picosecond titanium sapphire lasers 1, 2; however, it can use any type of light sources that can emit pulsed lights with an equal period.

While the heating light L1 passes through the acousto-optic modulator 7, the heating light L1 is subject to the intensity modulation by a signal having a frequency of 1 MHz. The 1 MHz signal for the intensity modulation is supplied from a signal generator 17. The signal for the intensity modulation is also supplied to the reference signal input of the lock-in-amplifier 15. For the intensity modulation, this embodiment employs the acousto-optic modulator 7; however, it may use other devices, such as a mechanical type chopper, or an electro-optic modulator. Further, the embodiment uses 1 MHz for the modulation frequency, and it has to be lower than the repetition frequency of the pulse; for example, the modulation frequency of 500 kHz to 10 MHz is appropriate with respect to the pulse repetition frequency of 76 MHz.

The modulated heating light L1 is focused on the boundary 12c of the thin film 12b and the substrate 12a. On the other hand, the probe light L3 is focused on the surface of the thin film on the opposite side 11b of the area heated (see FIG. 1 and FIG. 2).

A detector 21 composed of a silicon photodiode detects the probe light L2 reflected on the surface of the sample 11b. The detected signal is sent to the signal input terminal of the lock-in-amplifier 15. The temperature change on the surface of the sample 11 contains the components that vary by 1

MHz resulting from the intensity modulation of the heating light L1. Therefore, the probe light L2 reflected on the surface of the sample also contains the periodical components of 1 MHz. The lock-in-amplifier 15 detects the alternating components of the probe light L3 synchronized with the intensity modulation frequency 1 MHz.

The temporal thermoreflectance profile proportional to the temperature change is recorded by controlling the delay of time for the probing light L2 reaching the sample 11 against the heating light L1. The delay time control is made possible by controlling the signal generator 3 in FIG. 1: The signal generator 3 is a sine wave generator that has two outputs, the output (1) and the output (2). Both the outputs deliver 76 MHz sine waves, and the phase difference between the two signals is made controllable. The timing of emitting the heating light pulse L1 is constant to the signal from the output 1, and the timing of emitting the probe light pulse is constant to the signal from the output (2). Therefore, if the phase of the output (2) to the output (1) in the signal generator 3 is varied, it will be possible to control the delay of time for the probing light pulse reaching the sample against the heating light pulse. The phase difference of 1° in the sine wave signal of 76 MHz corresponds to 36.4 picoseconds in terms of the time difference for reaching the sample.

EMBODIMENT

Figure 5:
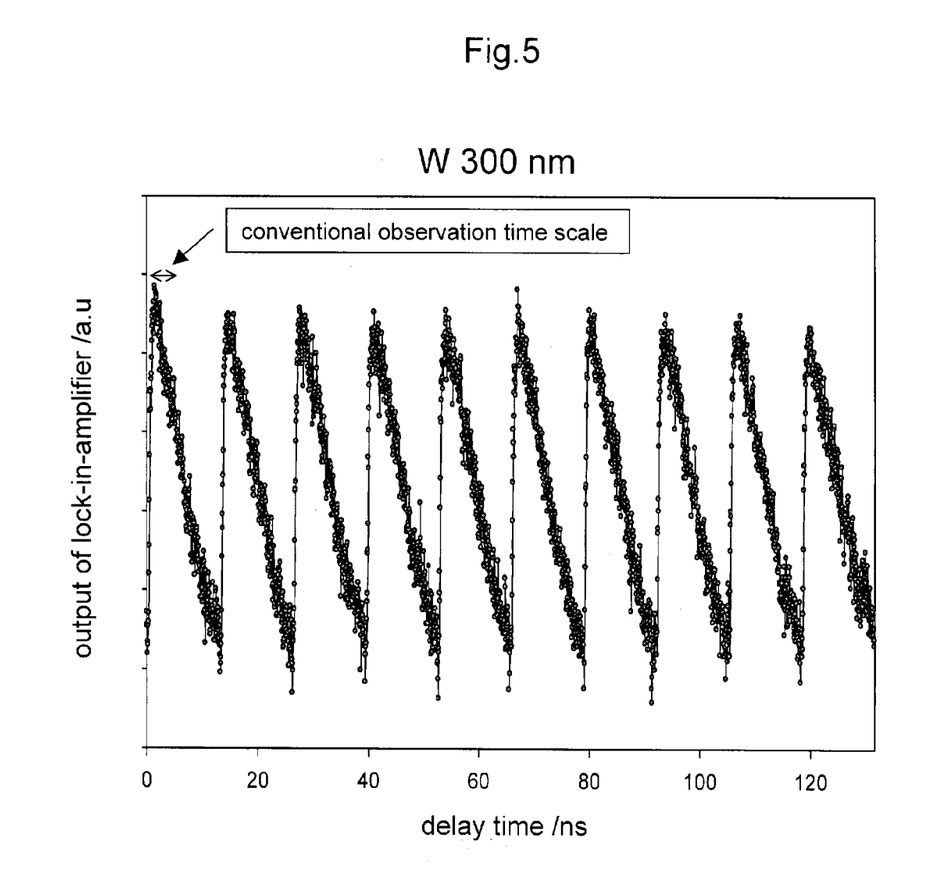
FIG. 5 illustrates a detection example of a signal when a tungsten thin film is measured by using the developed measurement system (observation time is 130 nanoseconds); and is

In order to verify that the developed measurement system is able to measure a longer delay time than the conventional measurement system, an actual measurement by the developed system was made which prepared for a tungsten thin film having the thickness of 300 nanometers, formed on a glass substrate by the spattering. FIG. 5 illustrates the phase components of the thermoreflectance signal of the tungsten thin film (in the picosecond thermoreflectance method, the change of the phase components against the delay time is known to be proportional to the surface temperature change by the pulse heating). The horizontal axis indicates the delay time of the probing light against the heating light, and the vertical axis indicates the phase components of the signal output from the lock-in-amplifier. The measured delay time is 130 nanoseconds, which corresponds to about 36000 in terms of the phase of the signal generator 3. FIG. 5 puts an arrow that shows a general time (1 ns) in the conventional system, for comparison' sake. FIG. 5 displays the state that the temperature response against the pulse heating is repeated by the repetition period (1/76 MHz=13.2 nanoseconds) of the heating light pulse. Thus, the developed system transcends the limitation of the observable time scale of the conventional system, and succeeds in observing the temperature response.

Figure 6:
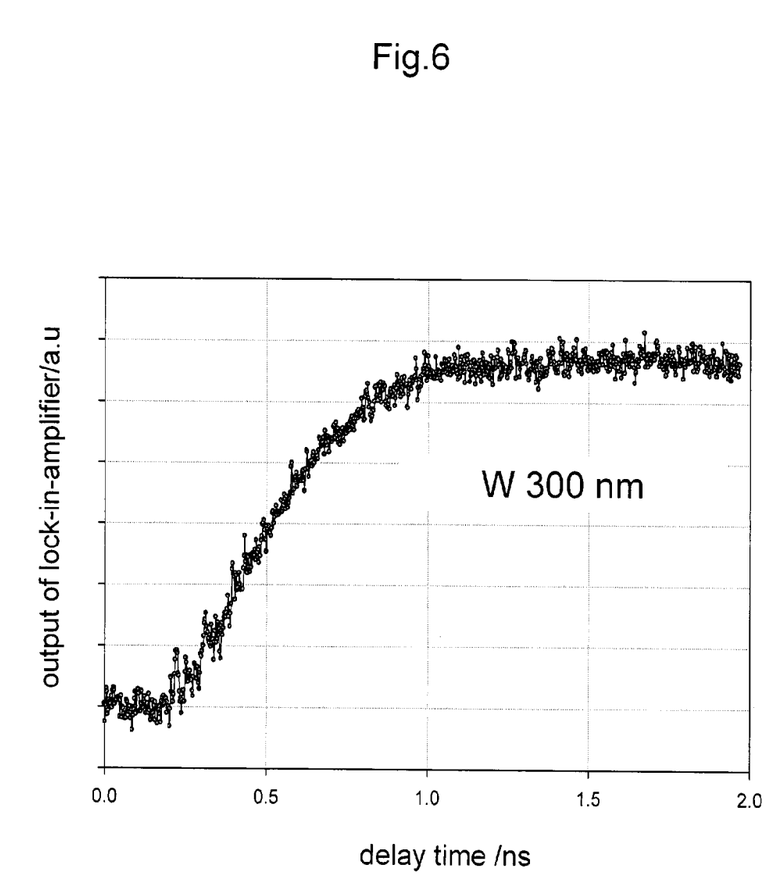
FIG. 6 illustrates a thermoreflectance signal when the tungsten thin film is measured by using the developed measurement system (observation time is 2 nanoseconds).

On the other hand, FIG. 6 illustrates the temperature response over 2 nanoseconds being comparable to the conventional measuring time scale. FIG. 6 confirms the state that the temperature rises with heat diffusion from the back of the film toward the front side. In this manner, the developed system is also capable of measuring the temperature response in the conventional time scale.

What is claimed is:

1. A method of measuring a fast time response of a sample by irradiating the sample using a fast pump light pulse, irradiating the sample using a probe light pulse, and observing a change of the probe light pulse reflected by the sample, corresponding to a response of the sample to the pump light pulse, said method comprising the steps of:

preparing a first light source that emits a light pulse periodically for exciting the sample as the pump light pulse, and preparing a second light source, separate from the first light source, that emits a light pulse with the same period as the pump light pulse as the probe light pulse; and electrically controlling a time difference between a time at which the pump light pulse irradiates the sample and a time at which the probe light pulse irradiates the sample, thereby detecting a signal representative of the observed change based on the probe light pulse reflected by the sample, wherein the detected signal varies depending on the time difference of the pump light pulse and the probe light pulse, wherein temperature rise of the sample is detected by a thermoreflectance method, and wherein, in order to measure with high sensitivity a thermoreflectance signal, an intensity of the pump light pulse oscillated periodically per pulse is modulated with a slower period, and an intensity component of a signal synchronized with the slower period is lock-in detected.

2. A method as claimed in claim 1, wherein a laser that periodically emits a light pulse is used for each of the two light sources, thereby providing a pump pulse laser and a probe pulse laser.

3. A method as claimed in claim 1, wherein the pulse widths of the first and second light sources are shorter than one nanosecond.

4. A method as claimed in claim 2, wherein the emitting period of the pump and probe pulse lasers is implemented by an electrical periodic reference signal.

5. A method as claimed in claim 2, further comprising the steps of:

synchronizing a periodic reference signal to be sent to the pump pulse laser for exciting the sample with another periodic reference signal to be sent to the probe pulse laser; and controlling a phase difference between the periodic reference signals to thereby control a time difference of irradiation between the pump light pulse and the probe light pulse.

6. A method as claimed in claim 1, wherein a temperature of the sample rises by a light pulse excitation.

7. A method as claimed in claim 1, wherein a change in the detected signal corresponds to a temperature change by thermal diffusion.

8. A method as claimed in claim 1, wherein the pump light pulse is irradiated on a surface of the sample, and a temperature rise of a front surface of the sample is detected.

9. A method as claimed in claim 1, wherein the sample is a single layer thin film or a multi-layered film.

10. A method as claimed in claim 1, wherein thermophysical properties including thermal diffusivity, boundary thermal resistance, and thermal effusivity are measured from the detected signal.

11. A method as claimed in claim 1, wherein the pump light pulse is irradiated on a surface of the sample, and a temperature rise of a back surface of the sample is detected.

12. A method as claimed in claim 1, wherein a phase component of the lock-in detected signal is used for measuring the change in intensity of a reflected signal from the sample.

13. A method as claimed in claim 1, wherein a phase component of the detected signal is measured, said phase component being representative of a heat response inside a thin film of the sample.

14. A method of measuring a fast time response using a fast pulse, as claimed in claim 1, wherein each laser periodically emits a light pulse.

15. A method of measuring a fast time response using a fast pulse, as claimed in claim 2, wherein each laser periodically emits a light pulse.

16. A method of measuring a fast time response using a fast pulse, as claimed in claim 2, wherein the pulse widths of the two light sources are shorter than one nanosecond.

17. A method of measuring a fast time response using a fast pulse, as claimed in claim 2, wherein the pump light pulse is irradiated on the surface of the sample, and the temperature rise of the front surface of the sample is detected.

18. A method of measuring a fast time response using a fast pulse, as claimed in claim 2, wherein the pump light pulse is irradiated on the surface of the sample, and the temperature rise of the back surface of the sample is detected.

19. A method of measuring a fast time response using a fast pulse, as claimed in claim 2, wherein the sample is a single layer thin film or a multi-layered film.

20. A method of measuring a fast time response using a fast pulse, as claimed in claim 2, wherein the thermophysical properties such as thermal diffusivity, boundary thermal resistance, thermal effusivity are measured from an observed signal.

21. A method of measuring a fast time response of a sample by irradiating the sample using a fast pulse of pump light, irradiating the sample using a probe light pulse, and observing a change of the probe light pulse reflected by the sample, corresponding to a response of the sample by the pump light pulse, said method comprising the steps of:
    preparing for a first light source that emits a light pulse periodically for exciting the sample as the pump light pulse, and preparing a second light source, separate from the fast light source, that emits a light pulse with the same period as the pump light pulse, as the probe light pulse; and
    electrically controlling a time difference between a time at which the pump light pulse irradiates the sample and a time at which the probe light pulse irradiates the sample, and thereby detecting a signal representative of the observed change based on the probe light pulse reflected by the sample,
    wherein the detected signal varies depending on the time difference of the pump light pulse and the probe light pulse,
    wherein temperature rise of the sample is detected by a thermoreflectance method, and
    wherein, in order to measure with high sensitivity a thermorefectance signal, an intensity of the pump light pulse oscillated periodically per pulse is modulated with a slower period, and a phase component of a signal synchronized with the slower period is lock-in detected.

22. A system for measuring a fast time response of a sample by irradiating the sample using a fast pump light pulse, irradiating the sample using a probe light pulse, and observing a change of the probe light pulse reflected by the sample, corresponding to a response of the sample to the pump light pulse, said system comprising:
    a first light source that emits a light pulse periodically for exciting the sample as the pump light pulse;
    a second light source that emits a light pulse with the same period as the pump light pulse as the probe light pulse;
    a controller that electrically controls a time difference between a time at which the pump light pulse irradiates the sample and a time at which the probe light pulse irradiates the sample; and
    a detector that detects a signal representative of the observed change based on the probe light pulse reflected by the sample,
    wherein the detected signal varies dependently on the time difference of the pump light pulse and the probe light pulse,
    wherein temperature rise of the sample is detected by a thermoreflectance method, and
    wherein, in order to measure with high sensitivity a thermoreflectance signal, an intensity of the pump light pulse oscillated periodically per pulse is modulated with a slower period, and an intensity component of a signal synchronized with the slower period is lock-in detected.

23. A system as claimed in claim 22, wherein a laser that periodically emits a light pulse is used for each of the first and second light sources, thereby providing a pump pulse laser and a probe pulse laser.

24. A system as claimed in claim 23, wherein the emitting period of the pump and probe pulse lasers is implemented by an electrical periodic reference signal.

25. A system as claimed in claim 23, further comprising:
    means for synchronizing a periodic reference signal to be sent to the pump pulse laser for exciting the sample with another periodic reference signal to be sent to the probe pulse laser, and controlling a phase difference between the periodic reference signals to thereby control a time difference of irradiation between the pump light pulse and the probe light pulse.

26. A method as claimed in claim 22, wherein the pump light pulse is irradiated on a surface of the sample, and a temperature rise of a front surface of the sample is detected.

27. A system as claimed in claim 22, wherein the sample is a single layer thin film or a multi-layered film.

28. A system as claimed in claim 22, wherein thermophysical properties including thermal diffusivity, boundary thermal resistance, and thermal effusivity are measured from the detected signal.

29. A method as claimed in claim 22, wherein the pump light pulse is irradiated on a surface of the sample, and a temperature rise of a back surface of the sample is detected.

30. A system for measuring a fast time response of a sample, by irradiating the sample using a fast pump light pulse, irradiating the sample using a probe light pulse, and observing a variation of the probe light pulse reflected by the sample, corresponding to a change in state of the sample caused by the pump light pulse, said system comprising:
    a first light source that emits a light pulse periodically for exciting the sample as the pump light pulse,
    a second light source that emits a light pulse with the same period as the pump light pulse as the probe light pulse;
    a controller that electrically controls a difference between a time at which the pump light pulse irradiates the sample and a time at which the probe light pulse irradiates the sample;

a detector that detects a signal representative of the variation in the probe light pulse reflected by the sample, wherein the detected signal varies dependently on a time difference between the pump light pulse and the probe light pulse, a laser periodically emits a light pulse which is used for each of the first and second light sources, thereby providing a pump pulse laser and a probe pulse laser, and an emitting period of the pump and probe pulse lasers is implemented by an electrical periodic reference signal, wherein a periodic reference signal to be sent to the pump pulse laser for exciting the sample is synchronized with a periodic reference signal to be sent to the probe pulse laser, and a phase difference between the periodic reference signals is controlled to thereby control a time difference of irradiation between the pump light pulse and the probe light pulse, wherein temperature rise of the sample is detected by a thermoreflectance method, and wherein, in order to measure with high sensitivity a thermoreflectance signal, an intensity of the pump light pulse oscillated periodically per pulse is modulated with a slower period, and an intensity component of a signal synchronized with the slower period is lock-in detected.

* * * * *